(12) United States Patent
Prisinzano

(10) Patent No.: US 9,428,494 B2
(45) Date of Patent: Aug. 30, 2016

(54) THERAPEUTIC COMPOUNDS

(75) Inventor: Thomas Prisinzano, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 880 days.

(21) Appl. No.: 12/513,093

(22) PCT Filed: Nov. 2, 2007

(86) PCT No.: PCT/US2007/083485
§ 371 (c)(1),
(2), (4) Date: Mar. 3, 2010

(87) PCT Pub. No.: WO2008/055261
PCT Pub. Date: May 8, 2008

(65) Prior Publication Data
US 2010/0179217 A1 Jul. 15, 2010

Related U.S. Application Data

(60) Provisional application No. 60/856,141, filed on Nov. 2, 2006.

(51) Int. Cl.
*A01N 43/16* (2006.01)
*C07D 407/04* (2006.01)

(52) U.S. Cl.
CPC .................. *C07D 407/04* (2013.01)

(58) Field of Classification Search
CPC .............................................. C07D 407/04
USPC ........................................................ 514/455
See application file for complete search history.

(56) References Cited

U.S. PATENT DOCUMENTS

2006/0052439 A1   3/2006   Beguin et al.

FOREIGN PATENT DOCUMENTS

WO   WO 2006/031782 A2   3/2006

OTHER PUBLICATIONS

Dorwald F. A. Side Reactions in Organic Synthesis, 2005, Wiley: VCH, Weinheim p. IX of Preface p. 1-15.*
Venkatesh et al., J. Pharm. Sci. 89, 145-54 (2000).*
Prisinzano and Rothman, Chem. Rev. 2008, 108, 1732-1743.*
Cunningham et al., Pharmacology Review, 2011, 62(3): 316-317.*
Holden et al. Bioorganic and Medicinal Chemistry Letters, 2007, 17, 6111-61115.*
Vortherms et al. Molecular Interventions, 2006, 6(5), 257-265.*
Patent Cooperation Treaty, International Search Report and Written Opinion of the International Search Authority, PCT/US07/83485, Jul. 31, 2008, 10 pages.
Alvarez, V., et al., "A RAVE about Opioid Withdrawal", *Neuron*, 32, 761-763, 2001.
Bailey, C. P., et al., "µ-Opioid Receptor Desensitization in Mature Rat Neurons: Lack of Interaction between DAMGO and Morphine", *J. Neuroscience*, 23(33), 10515-20, 2003.
Bohn, L. M., et al., "Mitogenic Signaling via Endogenous κ-Opioid Receptors in C6 Glioma Cells: Evidence for the Involvement of Protein Kinase C and the Mitogen-Activated protein Kinase Signaling Cascade", *J. Neurochem*, 74, 564-573, 2000.
Bohn, L. M., et al. "µ-Opioid receptor desensitization by β-arrestin-2 determines morphine tolerance but not dependence", *Nature*, 408, 720-723, 2000.
Bohn, L. M., et al. "Differential Mechanisms of Morphine Antinociceptive Tolerance Revealed in βArrestin-2 Knock-Out Mice", *J. Neuroscience*, 22(23), 10494-10500, 2002.
Bohn, L. M., et al. "Relative Opioid Efficacy is Determined by the Complements of the G Protein-Coupled Receptor Desensitization Machinery", *Mol. Pharmacology*, 66, 106-112, 2004.
Bohn, L. M., et al., "G Protein-Coupled Receptor Kinase/β-Arrestin Systems and Drugs of Abuse", *Neuromolecular Med.*, 5, 41-50, 2004.
Bohn, L. M., et al., "Enhanced Morphine Analgesia in Mice Lacking β-Arrestin 2", *Science*, 286, 2495-8, 1999.
Casy et al., "Opioid Analgesics: Chemistry and Receptors", *Plenum Press: New York*, xv, p. 518, 1986.
Connor, M., et al., "µ-Opioid receptor desensitization: Is morphine different?", *British J. Pharmacol.*, 143, 685-696, 2004.
Cunningham, C.W. et al., "Neuropharmacology of the Naturally Occurring κ-Opioid Hallucinogen Salvinorin A", *Pharm. Rev.* 62(3), pp. 316-347, 2011.
De Costa, B. R., et al., "Probes for Narcotic Receptor Mediated Phenomena. 18.[1]. Epimeric 6α- and 6β-Iodo-3,14-dihydroxy-17-(cyclopropylmethyl)-4,5α-epoxymorhinans as Potential Ligands for Opioid Receptor Single Photon Emission Computed Tomography: Synthesis, Evaluation, and Radiochemistry of [$^{125}$I]-6β-Iodo-3,14-dihydroxy-17-(cyclopropylmethyl)-4,5α-epoxymorhinan", *J. Med. Chem.*, 35, 2826-2835, 1992.

(Continued)

*Primary Examiner* — Nizal Chandrakumar
(74) *Attorney, Agent, or Firm* — Viksnins Harris & Padys PLLP

(57) ABSTRACT

The invention provides novel compounds of formula I: that are opioid receptor ligands. The invention also provides pharmaceutical compositions comprising such compounds as well as methods for treating diseases associated with opioid receptor function by administering such compounds to a mammal in need of treatment. Compounds of the invention are useful to modulate (e.g. agonize or antagonize) opioid receptor function.

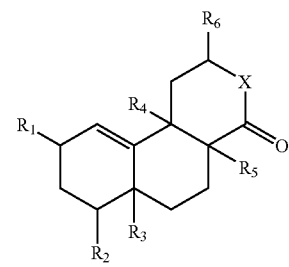

I

2 Claims, No Drawings

(56) References Cited

OTHER PUBLICATIONS

Detweiler, D. J., et al., "The development of opioid tolerance in the formalin test in the rat", *Pain*, 63, 251-254, 1995.
Dorwald, F.A., "Side Reactions in Organic Synthesis", 2005, Wiley: VCH, Weinheim p. IX of Preface p. 1-15.
Dubuisson, D., et al., "The Formalin Test: A Quantitative Study of the Analgesic Effects of Morphine, Meperidine, and Brain Stem Stimulation in Rats and Cats", *Pain*, 4, 161-174, 1977.
Eguchi, M., "Recent Advances in Selective Opioid Receptor Agonists and Antagonists", *Med. Res. Rev.*, 24, 182-212, 2004.
Fazli-Tabaei, S., et al., "Cross-tolerance between antinociception induced by swim-stress and morphine in formalin test", *Behav. Pharmacol.* 16, 613-619, 2005.
Gainetdinov, R. R., et al. "Desensitization of G Protein-Coupled Receptors and Neuronal Functions", *Annu. Rev. Neurosci.*, 27, 107-144, 2004.
Gay, E., et al., "Functional Selectivity of $D_2$ Receptor Ligands in a Chinese Hamster Ovary $hD_{2L}$ Cell Line: Evidence for Induction of Ligand-Specific Receptor States", *Mol. Pharmacol.*, 66, 97-105, 2004.
Gertrudes, A-S, "Tinophyllone, a Diterpenoid from *Tinomiscium philippinense* Diels", *Chemistry and Industry*, 25, 1074-1075, (1965). Specific CAS Registry No. 2749-27-1.
Goldstein, A., et al., "Multiple Opioid Receptors: Ligand Selectivity Profiles and Binding Site Signatures", *Mol. Pharmacol.*, 36, 265-272, 1989.
Gutstein, H., et al., "Opioid Analgesics", *Goodman & Gilman's The Pharmacological Basis of Therapeutics; 10th ed.*, McGraw-Hill: New York, 2001, pp. 569-619.
Haberstock-Debic, H., et al., "Morphine Acutely Regulates Opioid Receptor Trafficking Selectively in Dendrites of Nucleus Accumbens Neurons", *J. Neurosci.*, 23(10), 4324-4332, 2003.
Haberstock-Debic, H., et al., "Morphine Promotes Rapid, Arrestin-Dependent Endocytosis of μ-Opioid Receptors in Striatal Neurons", *J. Neurosci.*, 25(34), 7847-7857, 2005.
Harding, W. W., et al., "Neoclerodane Diterpenes as a Novel Scaffold for μ Opioid Receptor Ligands", *J. Med. Chem.*, 48, 4765-4771, 2005.
Holden, et al., "Synthetic studies of neoclerodane diterpenes from *Salvia divinorum*: Expoloration of the 1-position", *Bioorganic & Medicinal Chemistry Letters 17*, 2007, pp. 6111-6115.
Hunskaar, S., et al., "The formalin test in mice: dissociation between inflammatory and non-inflammatory pain", *Pain*, 30, 103-114, 1987.
Kaczor, A., et al., "Non-peptide Opioid Receptor Ligands—Recent Advances. Part II—Antagonists", *Curr. Med. Chem.*, 9, 1591-1603, 2002.
Kaczor, A., Non-peptide Opioid Receptor Ligands—Recent Advances. Part I—Agonists., *Curr. Med. Chem.*, 9, 1567-1589, 2002.
Kaneko, M., et al., "Role of Spinal Y-Aminobutyric Acid$_A$ Receptors in Formalin-Induced Nociception in the Rat", *J. Pharmacol. Exp. Ther.*, 282, 928-938, 1997.
Keith, D. E., et al., "Morphine Activates Opioid Receptors without Causing Their Rapid Internalization", *J. Biol. Chem.*, 271, 19021-19024, 1996.
Koch, T. et. al., "C-terminal Splice Variants of the Mouse μ-Opioid Receptor Differ in Morphine-induced Internalization and Receptor Resensitization", *J. Biol. Chem.*, 276, 31408-31414, 2001.
Koch, T., et al., "Receptor Endocytosis Counteracts the Development of Opioid Tolerance", *Mol. Pharmacol.*, 67, 280-287, 2005.
Koreeda et al., "The absolute stereochemistry of salvinorins", *Chemistry Letters*, 11, pp. 2015-2018, 1990.
Lu, Y., et al., "Stereospecific Synthesis of (2S)-2-Methyl-3-(2',6'-dimethyl-4'-hydroxyphenyl)-proprionic acid (Mdp) and its Incorporation Into an Opioid Peptide", *Biorg. Med. Chem. Lett.*, 11, 323-325, 2001.
Mansour, A., et al., "Opioid-receptor mRNA expression in the rat CNS: anatomical and functional implications", *Trends Neurosci.*, 18, 22-29, 1995.

Munro, T. A., et al., "Studies toward the Pharmacophore of Salvinorin A, a Potent κ Opioid Receptor Agonist", *J. Med. Chem.*, 48, 345-348, 2005.
Ni, Q., et al., "Selective Labeling of $κ_2$ Opioid receptors in Rat Brain by [$^{125}$I]IOXY: Interaction of Opioid Peptides and Other Drugs With Multiple $κ_{2a}$ Binding Sites", *Peptides*, 14, 1279-1293, 1993.
Oakley, R. H., et al., "Molecular Determinants Underlying the Formation of Stable Intracellular G Protein-coupled Receptor-β-Arrestin Complexes after Receptor Endocytosis", *J. Biol. Chem.*, 276, 19452-60, 2001.
Ortega, A., et al., "Salvinorin, a New *trans*-Neoclerodane Diterpene from *Salvia divinorum* (Labiatae)", *J. Chem. Soc. Perkin Trans.* 1, 2505-2508, 1982.
Pan, Y. X., et al., "Identification and Characterization of Three New Alternatively Spliced μ-Opioid Receptor Isoforms", *Mol. Pharmacol.*, 56, 396-403, 1999.
Pan, Z. Z., "μ-Opposing actions of the κ-opioid receptor", *TiPS*, 19, 94-98, 1998.
Pierce, K. L. et al., "Classical and New Roles of β-Arrestins in the Regulation of G-Protein-Coupled Receptors", *Nature Reviews Neuroscience*, 2, 727-733, 2001.
Prisinzano, et al., "Salvinorin A Analogs as Probes in Opioid Pharmacology", *Chem. Rev. 108*, pp. 1732-1743, 2008.
Przewlocka, B., et al., "Knockdown of spinal opioid receptors by antisense targeting β-arrestin reduces morphine tolerance and allodynia in rat", *Neurosci. Lett.*, 325, 107-10, 2002.
Raehal, K. M., et al., "Morphine Side Effects in β-Arrestin 2 Knockout Mice", *J Pharmacol Exp Ther. 314*, 1195-201, 2005.
Raehal, K.M., et al., "Mu Opioid Receptor Regulation and Opiate Responsiveness", *AAPS Journal*, 7, E587-E591, 2005.
Rees, D. C., et al., "Opioid Receptors", *Comprehensive Medicinal Chemistry; Pergammon*: New York, 805-846, 1990.
Reisine, T., "Neurotransmitter Receptors V: Opiate Receptors", *Neuropharmacology*, 34, 463-472, 1995.
Roth, B. L., et al., "Salvinorin A: A potent naturally occurring nonnitrogenous κ opioid selective agonist", *Proc. Natl. Acad. Sci. USA*, 99, 11934-11939, 2002.
Schulz, S., et al., "Morphine induces terminal μ-opioid receptor desensitization by sustained phosphorylation of serine-375", *Embo J.*, 23, 3282-9, 2004.
Shenoy, S. K., et al., "Multifaceted roles of β-arrestins in the regulation of seven-membrane-spanning receptor trafficking and signalling", *Biochem. J.*, 375, 503-15, 2003.
Stein C., "Mechanisms of Disease, The Control of Pain in Peripheral Tissue by Opioids", *N. Engl. J. Med.*, 332, 1685-90, 1995.
Stein C., et al., "Attacking pain at its source: new perspectives on opioids", *Nature Medicine*, 9, 1003-1008, 2003.
Stein, C., et al., "Intrinsic mechanisms of Antinociception in Inflammation: Local Opioid Receptors and β-Endorphin", *J. Neuroscience*, 10, 1292-8, 1990.
Stein, C., et al., "Local Opioid Receptors Mediating Antinociception in Inflammation: Endogenous Ligands", *Prog. Clin. Biol. Res.*, 328, 425-7, 1990.
Surratt, C. K., et al., "μ Opiate Receptor Charged Transmembrane Domain Amino Acids are Critical for Agonist Recognition and Intrinsic Activity", *J. Biol. Chem.*, 269, 20548-20553, 1994.
Tidgewell, "Herkinorin Analogues with Differential β-Arrestin-2 Interactions", *J. Med. Chem.*, 51(8), pp. 2421-2431, 2008.
Valdes III, L. J., et al., "Divinorin A, a Psychotropic Terpenoid, and Divinorin B from the Hallucinogenic Mexican Mint *Salvia divinorum*", *J. Org. Chem.*, 49, 4716-4720, 1984.
Vortherms, T.A. et al., Salvinorin A: From Natural Product to Human Therapeutics. Mol. Interventions 6(5), pp. 257-265, 2006.
Waldhoer, M., et al., "Opioid Receptors", *Annu. Rev. Biochem 73*, 953-990, 2004.
Wang, Y., et al., "Comparison of Pharmacological Activities of Three Distinct κ Ligands (Salvinorin A, TRK-820 and 3FLB) on κ Opioid Receptors in Vitro and Their Antipruritic and Antinociceptive Activities in Vivo", *J. Pharmacol. Exp. Ther.*, 312, 220-230, 2005.

(56) References Cited

OTHER PUBLICATIONS

Wheeler-Aceto, et al., "Standardization of the rat paw formalin test for the evaluation of analgesics", *Psychopharmacology*, 104, 35-44, 1991.

Whistler, J. L., et al., "Morphine-activated opioid receptors elude desensitization by β-arrestin", *Proc. Natl. Acad. Sci. USA*, 95, 9914-9, 1998.

Xu, H., et al., "Opioid Peptide Receptor Studies. 14. Stereochemistry Determines Agonist Efficacy and Intrinsic Efficacy in the [$^{35}$S] GTP-γ-S Functional Binding Assay", *Synapse 39*, 64-69, 2001.

Zhang, J., et al., "Role for G protein-coupled receptor kinase in agonist-specific regulation of μ-opioid receptor responsiveness", *Proc. Natl. Acad. Sci. USA 95*, 7157-62, 1998.

* cited by examiner

THERAPEUTIC COMPOUNDS

RELATED APPLICATIONS

This application is a National Stage application under 35 U.S.C. 371 and claims the benefit of priority of International Application No. PCT/US2007/083485 having an International Filing Date of Nov. 2, 2007 which claims the benefit of priority of U.S. Application Ser. No. 60/856,141 filed on Nov. 2, 2006, which are hereby incorporated by reference herein in their entireties.

GOVERNMENT FUNDING

The invention described herein was made with government support under Grant Number DA018151-A2 awarded by the National Institute on Drug Abuse. The United States Government has certain rights in the invention.

BACKGROUND OF THE INVENTION

The opium poppy, Papaver somniferum, has been used for centuries for the relief of pain and to induce sleep (Casy, A. F.; Parfitt, R. T. Opioid analgesics: chemistry and receptors; Plenum Press: New York, 1986; xv, 518). Among the most important constituents in opium are the alkaloids morphine and codeine. Many of the agonists and antagonists derived from these alkaloids are essential for the practice of modern medicine. While many potent agonists are effective analgesics, they have undesirable side effects, such as tolerance, dependence, and respiratory depression. (Stein, C.; Schafer, M.; Machelska, H. *Nat. Med.* 2003, 9, 1003-1008).

Endogenous opioid peptides are known and are involved in the mediation or modulation of a variety of mammalian physiological processes, many of which are mimicked by opiates or other non-endogenous opioid ligands. Some of the processes that have been suggested include analgesia, tolerance and dependence, appetite, renal function, gastrointestinal motility, gastric secretion, respiratory depression, learning and memory, mental illness, epileptic seizures and other neurological disorders and cardiovascular responses.

Intensive research of the last two decades has given us a better understanding of opioid receptor structure, distribution, and pharmacology (Waldhoer, M.; Bartlett, S. E.; Whistler, J. L. *Annu. Rev. Biochem.* 2004, 73, 953-990). Three types of opioid receptors known as mu ($\mu$), delta, ($\delta$), and kappa ($\kappa$) and receptor subtypes have been identified, and the mRNA encoding these receptors has been isolated. There is substantial pharmacological evidence for subtypes of each (Reisine, T. Neurotransmitter Receptors V: Opiate Receptors. *Neuropharmacology* 1995, 34, 463-472). It has become clear that each receptor mediates unique pharmacological responses and is differentially distributed in the central nervous system (Goldstein, A.; Naidu, A., *Mol. Pharmacol.* 1989, 36, 265-272; and Mansour, A.; Fox, C. A.; Akil, H.; Watson, S. J., *Trends Neurosci.* 1995, 18, 22-29).

The endogenous ligands for the opioid receptors are neuropeptides (Casy, A. F.; Parfitt, R. T. Opioid analgesics: chemistry and receptors; Plenum Press: New York, 1986; xv, 518). To date, three families of endogenous opioid peptides have been identified. They are classified, $\beta$-endorphins, enkephalins, and dynorphins (Gutstein, H.; Akil, H. Opioid Analgesics. Goodman & Gilman's The Pharmacological Basis of Therapeutics; 10th ed.; McGraw-Hill: New York, 2001; pp 569-619; and Eguchi, M., *Med. Res. Rev.* 2004, 24, 182-212). Although most of these endogenous opioids have little selectivity for opioid receptors, it is generally accepted that $\beta$-endorphins, enkephalins, and dynorphins display greater affinity for $\mu$, $\delta$ and $\kappa$ receptors respectively.

There are several structural classes of nonpeptidic opioid receptor ligands (Eguchi, M., *Med. Res. Rev.* 2004, 24, 182-212; Kaczor, A.; Matosiuk, D., *Curr. Med. Chem.* 2002, 9, 1567-1589; and Kaczor, A.; Matosiuk, D., *Curr. Med. Chem.*, 2002, 9, 1591-1603). The oldest class of compounds are those derived from morphine. Examples of other structural classes include fentanyl, cyclazocine, SNC 80, U50, 488H, and 3FLB. The common structural motif in all of these ligands is the presence of a basic amino group.

Currently, there is a need for new opioid receptor ligands that have fewer side effects than known ligands. Such ligands would be useful for the treatment of diseases and conditions associated with the activity of opioid receptors. Such ligands would also be useful as pharmacological tools for the further study of opioid pharmacology.

SUMMARY OF THE INVENTION

The present invention provides compounds that act as opioid receptor ligands. Accordingly there is provided a compound of the invention which is a compound of formula I:

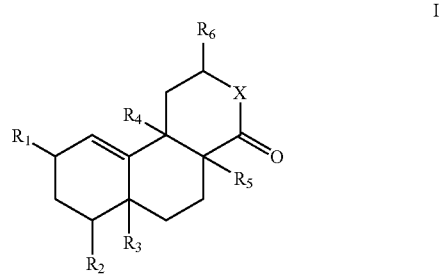

wherein:

$R_1$ is H, halo, azido, hydroxy, oxo (=O), $(C_1-C_6)$alkyl, $(C_1-C_6)$alkoxy, $(C_1-C_6)$alkylthio, $(C_1-C_6)$alkoxy$(C_1-C_6)$alkoxy, aryl, heteroaryl, aryloxy, heteroaryloxy, aryl$(C_1-C_6)$alkyl, aryl$(C_1-C_6)$alkoxy, heteroaryl$(C_1-C_6)$alkyl, heteroaryl $(C_1-C_6)$alkoxy, Het, Het$(C_1-C_6)$alkyl, Het$(C_1-C_6)$alkoxy, formyloxy, acetoxy, $R_cC(=O)O—$, $R_bC(=S)O—$, $R_bC(=O)S—$, $(R_g)_3SiO—$, $R_dR_eNC(=O)O—$, $(R_h)_3CC(=NR_d)O—$, $R_mR_nN—$, or $R_bS(=O)_2O—$;

$R_2$ is H, hydroxymethyl, $(C_1-C_6)$alkyl, $(C_1-C_6)$alkoxymethyl, carboxy, $(C_1-C_6)$alkoxycarbonyl or $R_dR_eNC(=O)—$;

$R_3$ is H or $(C_1-C_6)$alkyl;

$R_4$ is H or $(C_1-C_6)$alkyl;

$R_5$ is H or $(C_1-C_6)$alkyl;

$R_6$ is $(C_1-C_6)$alkyl, $(C_1-C_6)$cycloalkyl, aryl, Het, carboxy, $R_jR_kNC(=O)—$ or heteroaryl;

X is —O—, —S—, or —NR$_a$—;

each $R_a$ is independently H, $(C_1-C_6)$alkyl, aryl, heteroaryl, aryl$(C_1-C_6)$alkyl, or heteroaryl$(C_1-C_6)$alkyl;

each $R_b$ is independently H, $(C_1-C_6)$alkyl, $(C_2-C_6)$alkenyl, aryl, heteroaryl, aryl$(C_1-C_6)$alkyl, Het, Het$(C_1-C_6)$alkyl, or heteroaryl$(C_1-C_6)$alkyl;

each $R_c$ is independently H, $(C_2-C_6)$alkyl, $(C_2-C_6)$alkenyl, $(C_2-C_6)$alkoxycarbonyl, aryl, heteroaryl, aryl$(C_1-C_6)$alkyl, Het, Het$(C_1-C_6)$alkyl, or heteroaryl$(C_1-C_6)$alkyl;

each $R_d$ and $R_e$ is independently H, $(C_1-C_6)$alkyl, $(C_1-C_6)$alkenyl, aryl, heteroaryl, aryl$(C_1-C_6)$alkyl, or heteroaryl$(C_1-C_6)$alkyl;

each $R_g$ is independently $(C_1-C_6)$alkyl;

each $R_h$ is independently H, $(C_1-C_6)$alkyl, fluoro, or chloro;

each $R_j$ and $R_k$ is independently H, $(C_1-C_6)$alkyl, $(C_1-C_6)$alkenyl, aryl, heteroaryl, aryl$(C_1-C_6)$alkyl, Het, Het$(C_1-C_6)$alkyl, or heteroaryl$(C_1-C_6)$alkyl;

each $R_m$ and $R_n$ is independently H, $(C_1-C_6)$alkyl, $(C_1-C_6)$alkenyl, aryl, heteroaryl, aryloxy, heteroaryloxy, aryl$(C_1-C_6)$alkyl, aryl$(C_1-C_6)$alkoxy, heteroaryl$(C_1-C_6)$alkyl, heteroaryl$(C_1-C_6)$alkoxy, Het, Het$(C_1-C_6)$alkyl, Het$(C_1-C_6)$alkoxy, $(C_1-C_6)$alkanoyloxy, $R_pC(=O)-$, $R_dR_eNC(=O)-$, $(R_h)_3C(=NR_d)-$, or $R_bS(=O)_2-$; and each $R_p$ is independently H, $(C_1-C_6)$alkyl, $(C_2-C_6)$alkenyl, aryl, heteroaryl, aryl$(C_1-C_6)$alkyl, Het, Het$(C_1-C_6)$alkyl, or heteroaryl$(C_1-C_6)$alkyl;

wherein any aryl or heteroaryl of $R_1$, $R_6$, and $R_a-R_e$, and $R_p$ is optionally substituted with one or more (e.g. 1, 2, 3, or 4) halo, hydroxy, $(C_1-C_6)$alkyl, $(C_1-C_6)$alkoxy, $(C_1-C_6)$alkanoyloxy, $(C_1-C_6)$alkoxycarbonyl, cyano, nitro, trifluomethyl, trifluoromethoxy, $R_rS(=O)_2-$, or $R_uR_vN$;

each $R_t$ is independently H, $(C_1-C_6)$alkyl, $(C_2-C_6)$alkenyl, aryl, heteroaryl, aryl$(C_1-C_6)$alkyl, Het, Het$(C_1-C_6)$alkyl, or heteroaryl$(C_1-C_6)$alkyl;

wherein any aryl or heteroaryl of $R_t$ is optionally substituted with one or more (e.g. 1, 2, 3, or 4) halo, hydroxy, $(C_1-C_6)$alkyl, $(C_1-C_6)$alkoxy, $(C_1-C_6)$alkanoyloxy, $(C_1-C_6)$alkoxycarbonyl, cyano, nitro, trifluomethyl, trifluoromethoxy, or $R_uR_vN$;

wherein any Het of $R_1$, $R_6$, $R_b$, $R_c$, and $R_j-R_p$ is optionally substituted with one or more halo, hydroxy, $(C_1-C_6)$alkyl, $(C_1-C_6)$alkoxy, $(C_1-C_6)$alkanoyloxy, $(C_1-C_6)$alkoxycarbonyl, cyano, nitro, trifluomethyl, trifluoromethoxy, oxo (=O), thioxo (=S), $R_qS(=O)_2O-$, aryl, heteroaryl, or $R_uR_vN$;

each $R_q$ is independently H, $(C_1-C_6)$alkyl, $(C_2-C_6)$alkenyl, aryl, heteroaryl, aryl$(C_1-C_6)$alkyl, Het, Het$(C_1-C_6)$alkyl, or heteroaryl$(C_1-C_6)$alkyl; and each $R_u$ and $R_v$ is independently H or $(C_1-C_6)$alkyl;

or a salt thereof.

The invention also provides a pharmaceutical composition comprising a compound of formula I; or a pharmaceutically acceptable salt thereof; and a pharmaceutically acceptable diluent or carrier.

The invention also provides a method for modulating the activity of an opioid receptor comprising contacting the receptor (in vitro or in vivo) with an effective modulatory amount of a compound of formula I or a salt thereof.

The invention also provides a therapeutic method for treating a disease or condition in a mammal wherein modulation of the action of an opioid receptor is desired (e.g. pain, drug addiction, alcohol addiction, drug abuse, alcohol abuse, opioid-induced constipation, irritable bowel syndrome, nausea, vomiting, pruritic dermatoses, depression, smoking addiction, sexual dysfunction, stroke, obesity, diabetes, trauma, eating disorders, opioid overdose, shock, spinal damage, diarrheic syndromes, bowel motility disorders including post-operative ileus and constipation, visceral pain including post-operative pain, and inflammatory bowel disorders) comprising administering to the mammal, an effective amount of a compound of formula I; or a pharmaceutically acceptable salt thereof.

The invention also provides a compound of formula I or a pharmaceutically acceptable salt thereof for use in medical therapy.

The invention also provides the use of a compound of formula I or a pharmaceutically acceptable salt thereof to prepare a medicament useful for the treatment of a disease or condition in a mammal wherein modulation of the action of an opioid receptor is desired.

The invention also provides a method for binding a compound of formula I or a pharmaceutically acceptable salt thereof to mammalian tissue comprising opioid receptors, in vivo or in vitro, comprising contacting the tissue with an amount of a compound of formula I or a pharmaceutically acceptable salt thereof effective to bind to said receptors. Tissue comprising a compound of formula I or a pharmaceutically acceptable salt thereof bound to opioid receptor sites can be used to measure the selectivity of test compounds for specific receptor subtypes, or can be used as a tool to identify potential therapeutic agents for the treatment of diseases or conditions associated with opioid receptor activity, by contacting said agents with said ligand-receptor complexes, and measuring the extent of displacement of the ligand and/or binding of the agent.

The invention also provides a detectably labeled (e.g. a radiolabeled) compound comprising a compound of formula I; or a salt thereof, that comprises or is linked to one or more detectable groups.

The invention also provides synthetic processes and synthetic intermediates disclosed herein. Certain compounds of formula (I) are useful as intermediates for preparing other compounds of formula (I).

The invention also provides the compounds prepared in the Examples herein, as well as methods for modulating opioid receptor activity with such compounds.

DETAILED DESCRIPTION

The following definitions are used, unless otherwise described. Halo is fluoro, chloro, bromo, or iodo. Alkyl, alkoxy, etc. denote both straight and branched groups; but reference to an individual radical such as propyl embraces only the straight chain radical, a branched chain isomer such as isopropyl being specifically referred to.

Aryl denotes a phenyl radical or an ortho-fused bicyclic carbocyclic radical having about nine to ten ring atoms in which at least one ring is aromatic.

Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(Y) wherein Y is absent or is H, O, $(C_1-C_4)$alkyl, phenyl or benzyl, as well as a radical of an ortho-fused bicyclic heterocycle of about eight to ten ring atoms derived there from, particularly a benz-derivative or one derived by fusing a propylene, trimethylene, or tetramethylene diradical thereto.

"Het" includes a mono or bicyclic saturated or partially unsaturated ring system comprising about 4 to about 12 atoms selected from carbon, O, S, and N. Examples of "Het" include dihydrofuran, tetrahydrofuran, pyrazoline, piperidine, morpholine, thiomorpholine, piperazine, indoline, isoindoline, pyrazolidine, imidazoline, imidazolidine, pyrroline, pyrrolidine, chroman, and isochroman.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine opioid receptor binding and modulatory activity using the standard tests described herein, or using other similar tests which are well known in the art.

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for $R_1$ is H, halo, azido, hydroxy, $(C_1-C_6)$alkyl, $(C_1-C_6)$alkoxy, $(C_1-C_6)$alkylthio, $(C_1-C_6)$alkoxy$(C_1-C_6)$alkoxy, aryl, heteroaryl, aryloxy, heteroaryloxy, aryl$(C_1-C_6)$alkyl, aryl$(C_1-C_6)$alkoxy, heteroaryl$(C_1-C_6)$alkyl, heteroaryl$(C_1-C_6)$alkoxy, Het, Het$(C_1-C_6)$alkyl, Het$(C_1-C_6)$alkoxy, formyloxy, acetoxy, $R_cC(=O)O—$, $R_bC(=S)O—$, $R_bC(=O)S—$, $(R_g)_3SiO—$, $R_dR_eNC(=O)O—$, $(R_h)_3C(=NR_d)O—$, $R_mR_nN—$, or $R_bS(=O)_2O—$;

A specific value for $R_1$ is H, hydroxy, $(C_1-C_6)$alkyl, $(C_1-C_6)$alkoxy, aryl, heteroaryl, aryloxy, heteroaryloxy, aryl$(C_1-C_6)$alkyl, aryl$(C_1-C_6)$alkoxy, heteroaryl$(C_1-C_6)$alkyl, heteroaryl$(C_1-C_6)$alkoxy, formyloxy, $R_cC(=O)O—$, $(R_g)_3SiO—$, $R_dR_eNC(=O)O—$, $(R_h)_3C(=NR_d)O—$, or $R_bS(=O)_2O—$.

A specific value for $R_1$ is hydroxy, $(C_1-C_6)$alkoxy, aryloxy, heteroaryloxy, aryl$(C_1-C_6)$alkoxy, heteroaryl$(C_1-C_6)$alkoxy, formyloxy, acetoxy, $R_cC(=O)O—$, or $R_bS(=O)_2O—$.

A specific value for $R_1$ is formyloxy, acetoxy, $R_cC(=O)O—$, or $R_bS(=O)_2O—$.

A specific value for $R_1$ is acetoxy, propanoyloxy, isobutanoyloxy, methacryloyloxy, methoxyoxalyloxy, benzoyloxy, trimethylsilyloxy, imidazole-1-ylthiocarbonyloxy, methoxymethoxy, aminocarbonyloxy, butanoyloxy, pentanoyloxy, 1-bromobenzoyloxy, 2-bromobenzoyloxy, 3-bromobenzoyloxy, 4-methoxybenzoyloxy, 4-nitrobenzoyloxy, phenylsulfonyloxy, 4-methylphenylsulfonyloxy, 4-methoxyphenylsulfonyloxy, 4-bromophenylsulfonyloxy, (3-pyridylcarbonyloxy, methylsulfonyloxy, hydroxy, 1-imino-2,2,2-trichloroethoxy, phenylaminocarbonyloxy, allylaminocarbonyloxy, 3,4-dichlorobenzoyloxy, bromo, azido, amino, acetylamino, phenylcarbonylamino, methylsulfonylamino, phenylsulfonylamino, or benzoyloxy.

A specific value for $R_1$ is propanoyloxy, isobutanoyloxy, methacryloyloxy, methoxyoxalyloxy, 3-pyridylcarbonyloxy, methylsulfonyloxy, hydroxy, 1-imino-2,2,2-trichloroethoxy, phenylaminocarbonyloxy, allylaminocarbonyloxy, or benzoyloxy.

A specific value for $R_1$ is acetoxy, propanoyloxy, methylsulfonyloxy, or benzoyloxy.

A specific value for $R_1$ is benzoyloxy, 3-pyridylcarbonyloxy, or phenylaminocarbonyloxy.

A specific value for $R_2$ is hydroxymethyl, $(C_1-C_6)$alkoxymethyl, carboxy, $(C_1-C_6)$alkoxycarbonyl, or $R_dR_eNC(=O)—$.

A specific value for $R_2$ is carboxy, $(C_1-C_6)$alkoxycarbonyl; or $R_dR_eNC(=O)—$.

A specific value for $R_2$ is methoxycarbonyl.

A specific value for $R_4$ is H or methyl.

A specific value for $R_3$ is methyl.

A specific value for $R_4$ is methyl.

A specific value for $R_5$ is H.

A specific value for $R_5$ is methyl.

A specific value for $R_5$ is H.

A specific value for $R_6$ is aryl or heteroaryl, optionally substituted with one or more (e.g. 1, 2, 3, or 4) halo, hydroxy, $(C_1-C_6)$alkyl, $(C_1-C_6)$alkoxy, $(C_1-C_6)$alkanoyloxy, $(C_1-C_6)$alkoxycarbonyl, cyano, nitro, trifluomethyl, trifluoromethoxy, or $R_eR_fN$.

A specific value for $R_6$ is phenyl, thienyl, furanyl, pyrrolyl, or pyridyl, optionally substituted with one or more (e.g. 1, 2, 3, or 4) halo, hydroxy, $(C_1-C_6)$alkyl, $(C_1-C_6)$alkoxy, $(C_1-C_6)$alkanoyloxy, $(C_1-C_6)$alkoxycarbonyl, cyano, nitro, trifluomethyl, trifluoromethoxy, or $R_eR_fN$.

A specific value for $R_6$ is phenyl, or Het, optionally substituted with one or more (e.g. 1, 2, 3, or 4) halo, hydroxy, $(C_1-C_6)$alkyl, $(C_1-C_6)$alkoxy, $(C_1-C_6)$alkanoyloxy, $(C_1-C_6)$alkoxycarbonyl, cyano, nitro, trifluomethyl, trifluoromethoxy, or $R_eR_fN$.

A specific value for $R_6$ is 3-furyl, 3,4-dihydroxy-2,5-dimethoxytetrahydrofuran-3-yl, 2,5-dihydro-2,5-dimethoxyfuran-3-yl, carboxy, 2,5-dihydro-5-bromo-2-oxofuran-3-yl, 2-bromofuran-3-yl, 2,5-dimethoxytetrahydrofuran-3-yl, 1-methylsulfonylpyrrol-3-yl, 1-phenylsulfonylpyrrol-3-yl, 1-(4-methoxyphenyl)sulfonylpyrrol-3-yl, 1-(4-nitrophenyl)sulfonylpyrrol-3-yl, 3-pyrrolyl, 4-methoxycarbonylthiazol-2-yl, 4-methocycarbonyloxazol-2-yl, thiazol-2-yl, or oxazol-2-yl.

A specific value for $R_6$ is 3-furyl.

A specific value for X is $—O—$.

A specific value for $R_a$ is H, methyl, ethyl, phenyl, thienyl, furanyl, pyrrolyl, pyridyl, benzyl, phenethyl, thienylmethyl, furanylmethyl, pyrrolylmethyl, or pyridylmethyl.

A specific value for $R_b$ is H, methyl, ethyl, phenyl, thienyl, furanyl, pyrrolyl, pyridyl, benzyl, phenethyl, thienylmethyl, furanylmethyl, pyrrolylmethyl, or pyridylmethyl.

A specific value for $R_c$ is H, ethyl, phenyl, thienyl, furanyl, pyrrolyl, pyridyl, benzyl, phenethyl, thienylmethyl, furanylmethyl, pyrrolylmethyl, or pyridylmethyl.

A specific value for $R_d$ and $R_e$ is independently H, methyl, ethyl, phenyl, thienyl, furanyl, pyrrolyl, pyridyl, benzyl, phenethyl, thienylmethyl, furanylmethyl, pyrrolylmethyl, or pyridylmethyl.

A specific compound of formula (I) is a compound of formula (II):

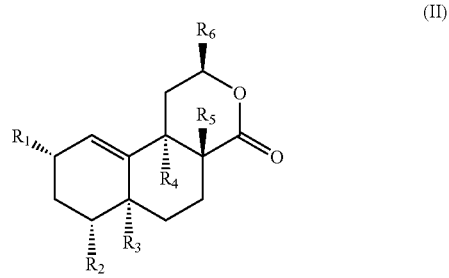

(II)

wherein R₁-R₆ have any of the values or specific values defined herein; or a salt thereof.

Specific compounds of the invention also include compounds of formula I that comprise or that are linked to one or more detectable groups or isotopes. Such detectable compounds may be used as imaging agents or as probes for evaluating opioid receptor structure and function. For example, one or more detectable groups can be incorporated into the core of the compound, or can be attached to the compound directly, through a linking group, or through a chelating group. Suitable detectable groups include deuterium, tritium, iodine-125, iodine-131, iodine-123, astatine-210, carbon-11, carbon-14, nitrogen-13, or fluorine-18. Additionally, groups such as Tc-99m and Re-186 can be attached to a linking group or bound by a chelating group which is then attached to the compound of formula I directly or by means of a linker. Suitable radiolabeling techniques are routinely used in radiopharmaceutical chemistry.

In one embodiment the invention also provides a compound of formula V:

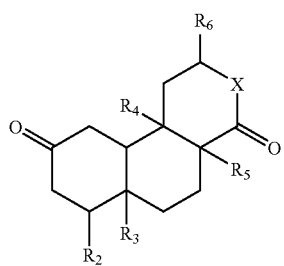

wherein R₂-R₆ and X have any of the values or specific values described herein. Compounds of formula V (e.g. Compound 8) are useful as intermediates for preparing salvinorin analogs.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes. For example, the compounds can be formulated for administration as a metered aerosol or liquid spray, as drops, in ampoules, in an autoinjector device or as suppositories; for oral parenteral, intranasal, sublingual or rectal administration, or for administration by inhalation or insufflation.

The compositions may be presented in a form suitable for once-weekly or once-monthly administration; for example, an insoluble salt of the active compound, may be adapted to provide a depot preparation for intramuscular injection. Furthermore, compounds of the invention can be administered in intranasal form via topical use of suitable intranasal vehicles, or via transdermal skin patches well known to those of ordinary skill in that art. To be administered in the form of a transdermal delivery system, the dosage administration will typically be continuous rather than intermittent throughout the dosage regimen.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be useful to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the useful methods of preparation include vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The compound can be administered in unit dosage form; for example, containing 5 to 1000 mg, 10 to 750 mg, or 50 to 500 mg of active ingredient per unit dosage form.

Ideally, the active ingredient should be administered to achieve peak plasma concentrations of the active compound of from about 0.5 to about 75 μM, about 1 to 50 μM, or about 2 to about 30 μM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Processes for preparing compounds of formula I are provided as further embodiments of the invention and are illustrated by the following procedures in which the meanings of the generic radicals are as given above unless otherwise qualified.

A compound of formula I can generally be prepared by as illustrated in the following Scheme I.

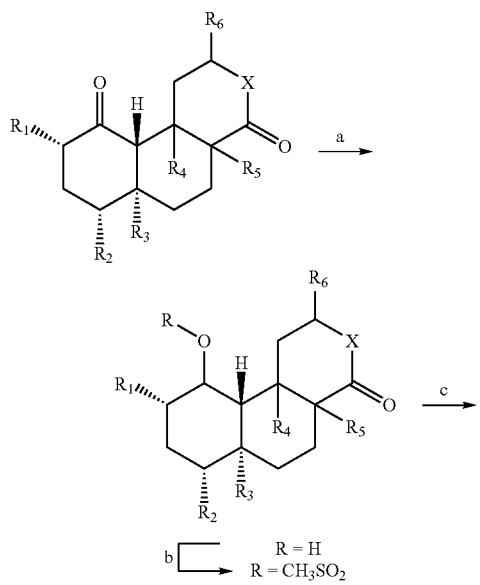

Scheme (I)

-continued

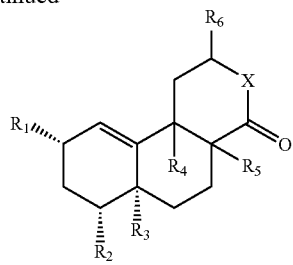

Reagents and conditions: (a) NaBH₄, THF/H₂O, Heat; (b) (CH₃SO₂)₂O, DMAP, CH₃CN, D; (c) PhN(CH₃)₃Cl, CH₃CN, Heat Compounds of the invention can also be administered in combination with other therapeutic agents, for example, other agents that are useful for the modulation of opioid activity. Examples of such agents include morphine, codeine, fentanyl, hydromorphone, naloxone, naltrexone, and nalmefene. Accordingly, in one embodiment, the invention also provides a composition comprising a compound of formula I, or a pharmaceutically acceptable salt thereof, at least one other therapeutic agent, and a pharmaceutically acceptable diluent or carrier. The invention also provides a kit comprising a compound of formula I, or a pharmaceutically acceptable salt thereof, at least one other therapeutic agent, packaging material, and instructions for administering the compound of formula I or the pharmaceutically acceptable salt thereof and the other therapeutic agent or agents to an animal to modulate opioid receptor activity.

The ability of a compound of the invention to act as a modulator of opioid receptor activity can be determined using pharmacological models which are well known to the art. For example, representative compounds of the invention were evaluated as described by Harding W W, et al., *J. Nat. Prod.* 2006, 69:107-112; and they were found to have opioid antagonist activity. Accordingly compounds of the invention may be useful as therapeutic agents for the treatment of diseases wherein the modulation of opioid activity is indicated. Such diseases include but are not limited to, pain, drug addiction, alcohol addiction, drug abuse, alcohol abuse, opioid-induced constipation, irritable bowel syndrome, nausea, vomiting, pruritic dermatoses, depression, smoking addiction, sexual dysfunction, stroke, obesity, diabetes, trauma, eating disorders, opioid overdose, shock, spinal damage, diarrheic syndromes, bowel motility disorders including post-operative ileus and constipation, visceral pain including post-operative pain, and inflammatory bowel disorders. Additionally, compounds of the invention may be useful as pharmacological tools for the further investigation of opioid receptor function.

The invention will now be illustrated by the following non-limiting Examples.

Unless otherwise indicated, all reagents were purchased from commercial suppliers and were used without further purification. All melting points were determined on a Thomas—Hoover capillary melting apparatus and are uncorrected. The $^1$H NMR and $^{13}$C NMR spectra were recorded at 300 MHz on a Bruker Avance-300 spectrometer or on a Bruker AMX-600 spectrometer using CDCl₃ as solvent, δ values in ppm (TMS as internal standard), and J(Hz) assignments of $^1$H resonance coupling. HMBC and HMQC data were collected on the AMX-600 spectrometer. Thin-layer chromatography (TLC) was performed on 0.25 mm Analtech GHLF silica gel plates. Spots on TLC were visualized with vanillin/H₂SO₄ in EtOH. Silica Gel (32-63µ particle size) from Bodman Industries (Atlanta, Ga.) was used for column chromatography. HPLC was carried out on an Agilent 1100 Series Capillary HPLC system with diode array detector. Peaks were detected at 209, 214 and 254 nm. MPLC was performed on a RT Scientific PurChrom 150-GCS system equipped with a silica gel column (1.1 cm×30 cm). Elemental analyses were performed by Atlantic Microlabs, Norcross, Ga.

Example 1

Preparation of 1-Deoxy-1,10-dehydro-salvinorin A (1)

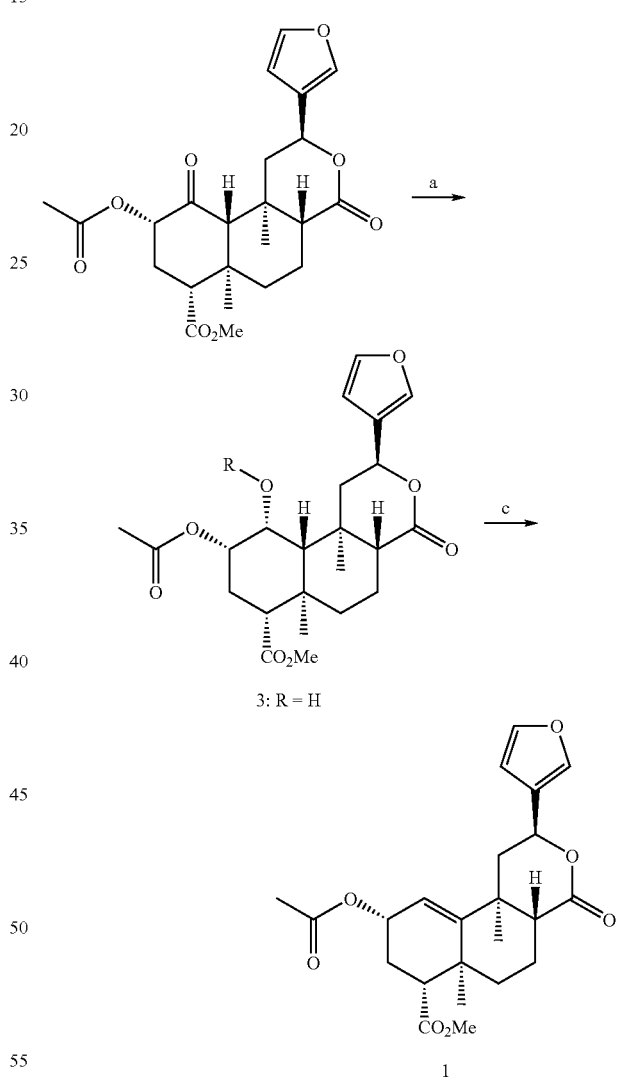

3: R = H

1

To a stirred solution of 1α-hydroxysalvinorin A (3, 291 mg, 0.67 mmol) and DMAP (488 mg, 4 mmol) in dry acetonitrile (6 mL) under argon was added methanesulfonic anhydride (313 mg, 1.8 mmoles). The reaction was stirred at reflux for 1 h, when complete conversion to the mesylate was indicated by TLC. This was followed by the addition of trimethyphenylammonium chloride (257 mg, 1.5 mmoles) and another 1 hour of reflux. The reaction mixture was evaporated and distributed between DCM (8 mL) and 1 M phosphoric acid (35 mL). The organic phase was washed with saturated sodium carbonate solution (20 mL), and the aqueous phases were extracted, in turn with DCM (2×4 mL). The combined and dried (sodium sulfate) organic phases were evaporated to a residue which was purified by column chromatography on silica gel (eluent: DCM/EtOAc, 9:1) gave Compound 1 (213 mg, 0.51 mmol, 76% overall). A portion of the product was recrystallized from EtOAc/hexanes to give pure material, mp 129-131° C.

The intermediate compound 3 was prepared as follows.

desired product (161 mg, 0.37 mmole, 9%) in which the acetate group has migrated from C-2 to C-1. A sample of the major product, 1α-hydroxy-SVA (3) was crystallized from EtOAc/hexanes, mp 110-111° C.

Example 2

Preparation of 1-Deoxy-1,10-dehydrosalvinorin B (2)

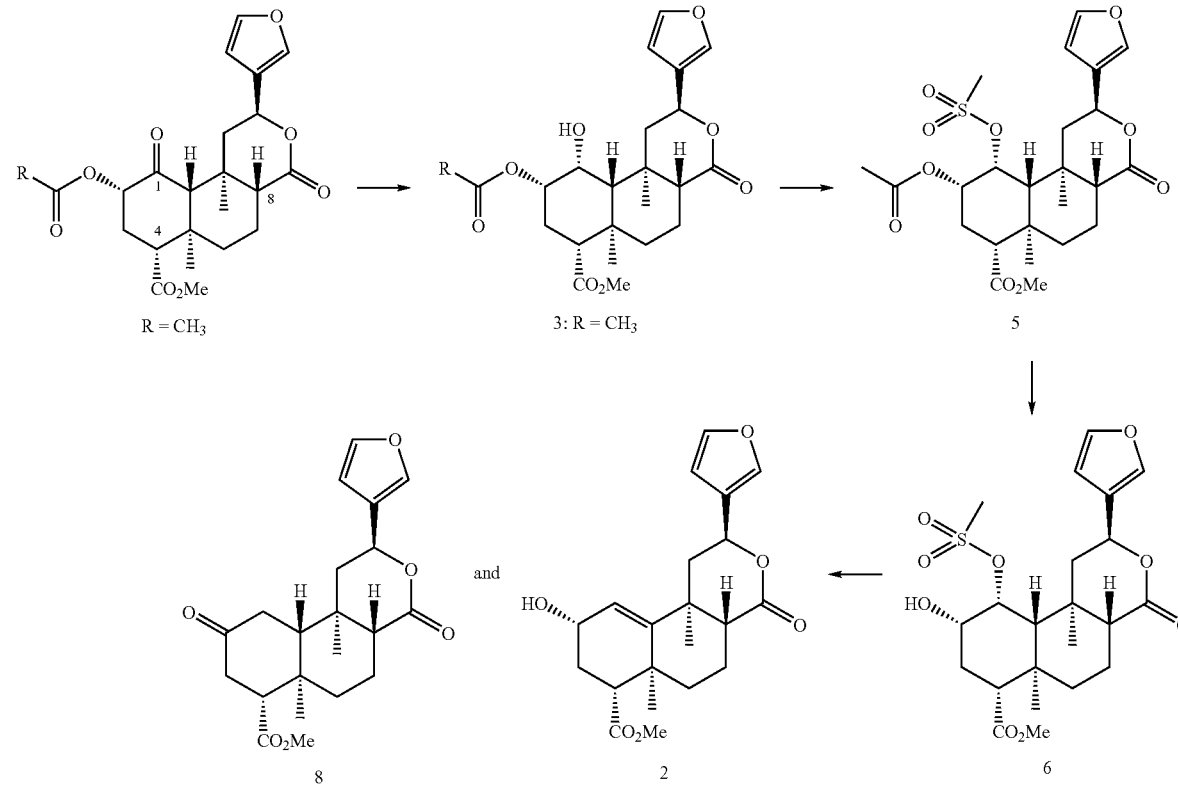

a. 1α-Hydroxy-Salvinorin A (3). A mixture of salvinorin A (1.7828 g, 4 mmol) and THF (40 mL) was magnetically stirred at gentle reflux for 5 minutes. To this was added an aqueous solution of sodium borohydride (760 mg, 20 mmoles in 6 mL) in portions. After stirring at reflux for 10 minutes following the first addition, a second addition of aqueous sodium borohydride was made (152 mg, 4 mmol in 0.7 mL) and reflux was continued for 5 minutes. The reaction mixture was immediately chilled in an ice bath and progress of the reaction was checked by TLC. The reaction was mixture diluted with ethyl acetate (50 mL) and extracted with saturated sodium chloride (2×30 mL). The aqueous phases were extracted, in turn, with ethyl acetate (2×15 mL) and the combined organic phases were dried (sodium sulfate) and evaporated to a foam (1.70 g). The crude product was chromatographed on silica (50 g) packed in DCM containing 10% EtOAc. Elution with DCM containing increasing amounts of EtOAc gave fractions that were combined based on TLC analysis. Early fractions contained the desired product (1.34 g, 3.08 mmoles, 77%) contaminated with a small amount of starting material, while later fractions contained lactols (158 mg, 0.36 mmole, 9%) reduced at C-17 as well as C-1, and finally an isomer of the A stirred solution of DMAP (122 mg, 1 mmole) in DMSO (3 mL) under argon was rapidly heated to 170° C. After 3 min, compound 6 (240 mg, 0.50 mmole) was added and stirring was continued for 10 min. The rapidly cooled reaction mixture was poured into a mixture of saturated aqueous NaCl (40 mL) and 1 M phosphoric acid (7 mL). The resulting aqueous mixture was extracted with EtOAc (20 mL) and the organic phase was washed with a mixture of saturated NaCl (20 mL) and saturated NaHCO$_3$ (7 mL). The aqueous phases were extracted, in turn, with EtOAc (10 mL). The combined organic phases were dried (Na$_2$SO$_4$) and evaporated to a residue (208 mg), which was purified by column chromatography, eluting with CH$_2$Cl$_2$ containing increasing amounts of EtOAc to afford 143 mg (76%) of 2 and 43 mg (22%) of 8.

1-Deoxy-1,10-dehydrosalvinorin B (2)

mp 121-122° C. (EtOAc/hexanes); $^1$H NMR (CDCl$_3$): δ 1.34 (s, 3H); 1.35 (s, 3H); 1.43 (dd, J=3.6, 13.5 Hz, 1H); 1.91 (m, 4H); 2.13 (m, 1H); 2.18 (m, 1H); 2.23 (dd, J=3.7, 6.5 Hz, 1H); 2.42 (d, J=13.5 Hz, 1H); 2.44 (dd, J=6.0, 13.5 Hz, 1H); 4.35 (m, 1H); 5.50 (d, J=2.1 Hz, 1H); 5.55 (dd, J=5.4, 12.0 Hz, 1H); 6.43 (dd, J=0.9, 1.8 Hz, 1H); 7.43 (dd, J=1.5, 1.8 Hz, 1H); 7.47 (dd, J=0.9, 1.5 Hz, 1H); $^{13}$C NMR (CDCl$_3$): δ 18.74, 21.98, 23.26, 31.14, 37.43, 38.58, 38.96, 43.15, 50.24, 51.81, 52.88, 67.53, 72.05, 108.67, 124.24, 125.79, 139.67, 144.04, 150.15, 172.47, 173.50

Compound 8 is an intermediate that is useful for preparing other salvinorin derivatives. 2-keto-1-deoxysalvinorin A (8). mp 227-228° C. (EtOAc/hexanes); $^1$H NMR (CDCl$_3$): δ 1.12 (s, 3H); 1.26 (s, 3H); 1.41 (dd, J=3.9, 12.9 Hz, 1H); 1.49 (dd, J=6.6, 8.1 Hz, 1H); 1.66 (m, 2H); 1.82 (dt, J=3.0, 13.5 Hz, 1H); 2.15 (dd, J=3.0, 6.0 Hz, 1H); 2.19 (dd, J=3.0, 5.4 Hz, 1H); 2.23 (dd, J=5.4, 13.5 Hz, 1H); 2.40 (s, 1H); 2.47 (m, 3H); 2.81 (dd, J=12.6, 15.0 Hz, 1H); 3.71 (s, 3H); 5.48 (dd, J=5.4, 11.4 Hz; 1H); 6.39 (dd, J=1.5, 1.5 Hz, 1H); 7.42 (m, 2H); $^{13}$C NMR (CDCl$_3$): δ 14.50, 14.52, 18.45, 36.62, 37.24, 3796, 38.23, 40.57, 43.70, 51.15, 52.09, 53.97, 55.13, 71.87108.56, 125.69, 139.55, 144.14, 171.65, 172.12, 208.16

The intermediate compound 6 was prepare as follows.

a. 1α-Hydroxysalvinorin A (3)

A mixture of salvinorin A (1.7828 g, 4 mmoles) and THF (40 mL) was magnetically stirred at gentle reflux for 5 min. To this was added an aqueous solution of NaBH$_4$ (760 mg, 20 mmoles in 6 mL) in portions. After stirring at reflux for 10 min following the first addition, a second addition of aqueous NaBH$_4$ was made (152 mg, 4 mmoles in 0.7 mL) and reflux was continued for 5 min. The reaction mixture was immediately chilled in an ice bath and progress of the reaction was checked by TLC. The reaction was mixture diluted with EtOAc (50 mL) and extracted with saturated sodium chloride (2×30 mL). The aqueous phases were extracted, in turn, with EtOAc (2×15 mL) and the combined organic phases were dried (Na$_2$SO$_4$) and evaporated to a foam. The crude product was purified by column chromatography (CH$_2$Cl$_2$ with increasing amounts of EtOAc) to give 1.34 g of 3 (77%) as a white solid, mp 110-111° C. The $^1$H and $^{13}$C spectra of 3 were in agreement with previously reported data (Valdes, L. J., III, et al., *J. Org. Chem.* 1984, 49, 4716).

b. 1α-Mesyloxysalvinorin A (5)

To a stirred solution of 3 (868 mg, 2 mmoles) in dry acetonitrile (10 mL) under argon was added DMAP (1.098 g, 9 mmoles) followed by methanesulfonic anhydride (696 mg, 4 mmoles). The reaction mixture was heated at reflux for 1 h. After cooling to room temperature, the reaction mixture was diluted with ethyl acetate (40 mL) and extracted with a mixture of 1 M phosphoric acid and saturated NaCl (40 mL, 1:1) followed by a mixture of saturated NaHCO$_3$ and saturated NaCl (30 mL, 1:2). The aqueous phases were extracted, in turn, with ethyl acetate (2×20 mL), and the combined organic phases were dried (Na$_2$SO$_4$) and evaporated to give 1.014 g (99%) of 5 as a foam. A sample was crystallized from CH$_2$Cl$_2$/EtOH to give pure 5, mp 190-194° C. (dec.); $^1$H NMR (CDCl$_3$): δ 1.26 (d, J=1.8 Hz, 1H); 1.32 (s, 3H); 1.43 (s, 3H); 1.58 (s, 3H); 1.69 (m, 2H); 1.89 (m, 2H); 2.08 (d, J=2.7 Hz, 1H); 2.11 (s, 3H); 2.16 (m, 1H); 2.30 (m, 1H); 2.31 (s, 1H); 2.49 (dd, J=5.4, 12.9 Hz, 1H); 3.23 (s, 3H); 3.71 (s, 3H); 4.80 (m, 1H); 5.36 (br s, 1H); 5.56 (dd, J=5.4, 11.4 Hz, 1H); 6.42 (dd, J=0.9, 1.5 Hz, 1H); 7.42 (dd, J=1.5, 1.8 Hz, 1H); 7.47 (dd, J=0.9, 1.8 Hz, 1H).

c. 1α-Mesyloxysalvinorin B (6)

A mixture of crude 5 (1.280 g, 2.5 mmoles) was stirred with DCM (2 mL) under argon and a solution of 1 drop of 50% aqueous sodium hydroxide in 8 mL of methanol was added quickly in portions. Crystals of starting material that initially appeared dissolved within 1-2 min and a heavy precipitate of product began to form. The reaction mixture was chilled to −10° C. and after 1 h was filtered to give 844 mg (70%) of 6 as a crystalline product. A sample was recrystallized from CH$_2$Cl$_2$/EtOH to give pure 6, mp 160-162° C. (dec.); $^1$H NMR (CDCl$_3$): δ 1.18 (s, 1H); 1.31 (s, 3H); 1.43 (s, 3H); 1.57 (s, 3H); 1.65 (m, 2H); 1.86 (m, 2H); 2.05 (m, 1H); 2.16 (m, 1H); 2.20 (s, 1H); 2.48 (d, J=5.4 Hz, 1H); 2.57 (dd, J=5.4, 13.2 Hz, 1H); 3.26 (s, 3H); 3.71 (s, 3H); 5.34 (br s, 1H); 5.55 (dd, J=5.4, 11.7 Hz, 1H); 6.41 (d, J=1.2 Hz, 1H); 7.42 (dd, J=1.5, 1.8 Hz, 1H); 7.46 (s, 1H); $^{13}$C NMR (CDCl$_3$): δ 16.17, 18.17, 18.72, 28.79, 37.39, 37.48, 39.88, 41.04, 43.90, 51.95, 53.12, 55.04, 55.23, 71.41, 71.94, 79.89, 108.61, 125.56, 139.75, 144.03, 172.47, 173.83

Example 3

Preparation of 2-keto-1-deoxy-1,10-dehydrosalvinorin A (9)

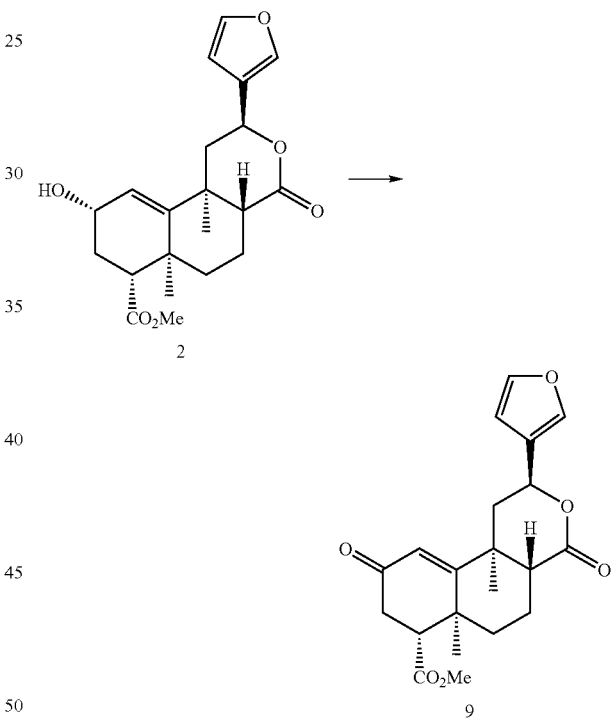

A mixture of compound 2 (253 mg, 0.68 mmole) and manganese dioxide (2 g) in toluene (10 mL) was heated at reflux for 20 min. This was followed by the addition of manganese dioxide (2 g), 20 min reflux, then manganese dioxide (1 g) and a further 20 min reflux. The hot mixture was filtered (filter aide) and the precipitate was washed with EtOAc. The filtrate was evaporated to give the product (198 mg, 0.53 mmole, 78%). A sample was recrystallized from EtOAc to give 9, mp 192-194° C. $^1$H NMR (CDCl$_3$): δ 1.41 (s, 3H); 1.48 (s, 3H); 1.63 (dd, J=0.9, 13.5 Hz, 1H); 1.90 (m, 2H); 2.02 (dd, J=1.2, 10.5 Hz, 1H); 2.33 (m, 2H); 2.52 (m, 2H); 2.90 (dd, J=14.4, 24 Hz, 1H); 2.93 (s, 1H); 3.73 (s, 3H); 5.58 (dd, J=5.4, 11.4 Hz, 1H); 5.94 (s, 1H); 6.42 (dd, J=0.9, 1.8 Hz, 1H); 7.44 (dd, J=1.8, 1.8 Hz, 1H); 7.47 (s, 1H); $^{13}$C NMR (CDCl$_3$): δ 18.22, 22.05, 22.51, 36.60, 37.51, 38.16, 39.86, 41.90, 49.19, 52.19, 52.91, 71.66, 108.54, 123.95, 125.37, 139.72, 144.24, 171.02, 172.10, 172.13, 197.68

Example 4

Preparation of 1-Deoxy-1,10-dehydroherkinorin (10)

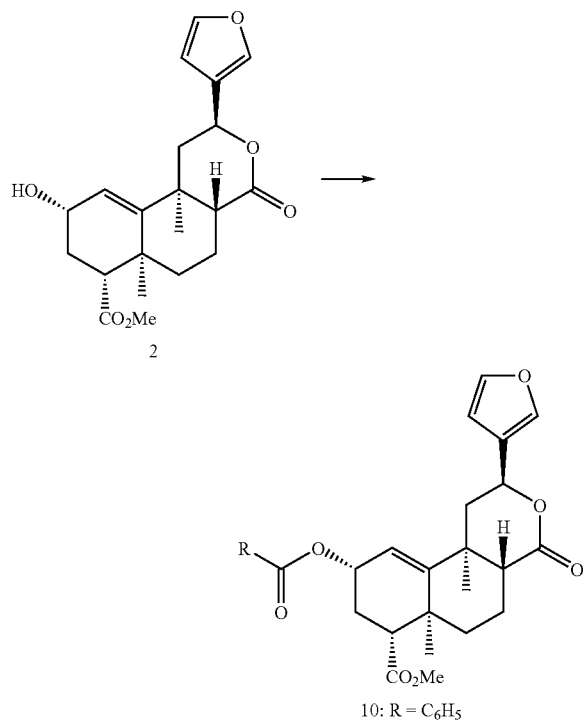

10: R = C₆H₅

A solution of 2 (0.050 g, 0.134 mmol), benzoyl chloride (0.056 g, 0.401 mmol), Net₃ (0.020 g, 0.200 mmol) and a catalytic amount of DMAP in $CH_2Cl_2$ (20 mL) was stirred at room temperature overnight. Absolute MeOH (15 mL) was added and the solvent was removed under reduced pressure. $CH_2Cl_2$ (25 mL) was added to the residue and the solution was washed with 2N HCl (3×30 mL), 2N NaOH (3×30 mL) and saturated NaCl (2×20 mL) and dried ($Na_2SO_4$). Removal of the solvent under reduced pressure to afford crude. The residue was purified by column chromatography (eluent: Hexanes/EtOAc, 7:3) to give 0.025 g (40%) of 10 as a white solid, mp 85-87° C.; $^1$H NMR ($CDCl_3$): δ 1.38 (s, 3H); 1.41 (s, 3H); 1.49 (dd, J=4.0, 13.0 Hz, 1H); 1.92 (m, 3H); 2.24 (m, 4H); 2.43 (dd, J=5.4, 13.5 Hz, 1H); 2.57 (dd, J=2.7, 13.2 Hz, 1H); 3.71 (s, 3H); 5.53 (dd, J=5.1, 11.4 Hz, 1H); 5.57 (s, 1H); 5.66 (m, 1H); 6.43 (dd, J=0.9, 1.8 Hz, 1H); 7.42 (dd, J=1.5, 1.8 Hz, 1H); 7.45 (d, J=0.9 Hz, 1H); 7.47 (dt J=0.6, 0.9, 2.4 Hz, 2H); 7.58 (tt, J=1.2, 1.5, 2.4, 7.2 Hz, 1H); 8.05 (dt, J=1.5, 1.8, 6.9 Hz, 2H); HRMS (m/z): [M+H]⁺ calcd for $C_{28}H_{30}O_7$, 478.1992. found, 478.2006.

Example 5

The following illustrate representative pharmaceutical dosage forms, containing a compound of formula I ('Compound X'), for therapeutic or prophylactic use in humans.

| (i) Tablet 1 | mg/tablet |
|---|---|
| Compound X= | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X= | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X= | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0-7.5) | q.s. |
| Water for injection | q.s. ad 1 mL |

| (vi) Aerosol | mg/can |
|---|---|
| Compound X= | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific embodiments and techniques.

However, it should be understood that many variations and modifications may be made while remaining within the spirit and scope of the invention.
What is claimed is:
1. A compound which is a compound of formula 1 or 2:
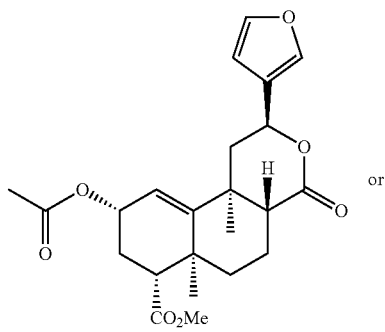
1
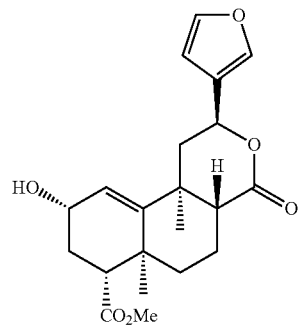
2
or a salt thereof.
2. A compound which is a compound of formula 9 or 10:
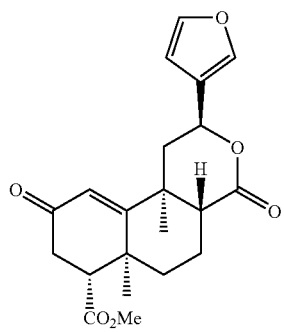
9
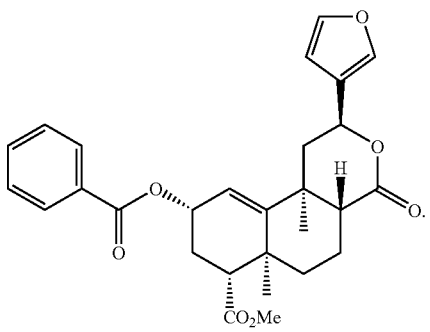
10
* * * * *

UNITED STATES PATENT AND TRADEMARK OFFICE
CERTIFICATE OF CORRECTION

PATENT NO.        : 9,428,494 B2
APPLICATION NO.   : 12/513093
DATED             : August 30, 2016
INVENTOR(S)       : Thomas E. Prisinzano Page 1 of 1

It is certified that error appears in the above-identified patent and that said Letters Patent is hereby corrected as shown below:

On the Title Page

Item (56), Other Publications, Cunningham et al., please delete "6111 – 61115.*" and insert -- 6111 – 6115.* -- therefor.

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*

UNITED STATES PATENT AND TRADEMARK OFFICE
CERTIFICATE OF CORRECTION

PATENT NO. : 9,428,494 B2
APPLICATION NO. : 12/513093
DATED : August 30, 2016
INVENTOR(S) : Thomas Prisinzano It is certified that error appears in the above-identified patent and that said Letters Patent is hereby corrected as shown below:

In the Specification

Column 1, Lines 15-18, GOVERNMENT FUNDING, please delete "The invention described herein was made with government support under Grant Number DA018151-A2 awarded by the National Institute on Drug Abuse. The United States Government has certain rights in the invention" and insert -- This invention was made with government support under DA018151 awarded by the National Institutes of Health. The government has certain rights in the invention. -- therefor.

Signed and Sealed this
Thirty-first Day of March, 2020

Andrei Iancu
*Director of the United States Patent and Trademark Office*